(12) United States Patent
Kolb

(10) Patent No.: US 6,929,664 B2
(45) Date of Patent: Aug. 16, 2005

(54) OPEN LUMEN STENTS

(75) Inventor: Gloria Ro Kolb, Quincy, MA (US)

(73) Assignee: Fossa Medical, Inc., Needham, MA (US)

( * ) Notice: Subject to any disclaimer, the term of this patent is extended or adjusted under 35 U.S.C. 154(b) by 0 days.

(21) Appl. No.: 10/731,262

(22) Filed: Dec. 5, 2003

(65) Prior Publication Data

US 2005/0125072 A1 Jun. 9, 2005

(51) Int. Cl.[7] ............................................... A61F 2/36
(52) U.S. Cl. ..................... 623/23.66; 623/23.7; 604/8; 264/211.12
(58) Field of Search ............................. 623/1.11, 23.7, 623/23.66, 23.64, 23.65; 604/8; 264/177.17, 264/209.1, 211.12

(56) References Cited

U.S. PATENT DOCUMENTS 5,282,784 A * 2/1994 Willard ........................ 604/8
6,214,037 B1 * 4/2001 Mitchell et al. ........... 623/1.11
6,524,268 B2 * 2/2003 Hayner et al. .................. 604/8

FOREIGN PATENT DOCUMENTS

WO    WO0189415 A3 * 11/2001

* cited by examiner

Primary Examiner—Corrine McDermott
Assistant Examiner—Thomas J Sweet
(74) Attorney, Agent, or Firm—Foley Hoag LLP; Scott E. Kamholz

(57) ABSTRACT

A stent may include a flexible, elongate body having a curled proximal portion, a curled distal portion, and a main portion extending between the proximal and distal portions. The main and distal portions together may define a channel laterally open throughout at least a part of the channel's length and extending along the main and distal portions without extending along the proximal portion, whereby the channel's proximal end is disposed in the main portion. In addition, the proximal portion may be curled away from the channel.

47 Claims, 6 Drawing Sheets

OPEN LUMEN STENTS

BACKGROUND

Stents are used in a wide variety of medical settings to prevent obstruction of body lumens. Stents facilitate fluid flow through body lumens by propping open the walls of the lumen and/or by providing an alternate lumen for fluid flow.

SUMMARY

The present disclosure is directed to stents of the type that includes a flexible, elongate body having a curled proximal portion, a curled distal portion, and a main portion extending between the proximal and distal portions. In one embodiment, the main and distal portions together define a channel that extends along the main and distal portions but stops short of the proximal portion; the channel's proximal end is disposed in the main portion. In addition, the proximal portion is curled away from the channel.

In another embodiment, the laterally open portion of the channel is so sized as to enable it to contain an object that cannot be laterally removed from the channel without expanding the channel's gap. In addition, the channel extends into the proximal portion and is laterally open throughout at least a part of the proximal portion, thereby defining a proximal lateral gap. Furthermore, the proximal lateral gap is larger than the channel's gap in the main and distal portions.

In yet another embodiment, the main and distal portions together define first and second channels that are separate from each other. Each channel is laterally open throughout at least a respective part of that channel's length and extends along the main and distal portions. At least the first channel stops short of the proximal portion, so that the first channel's proximal end is disposed in the main portion. Furthermore, the proximal portion is curled away from the channel through at least 270 degrees.

DETAILED DESCRIPTION

The disclosed stents facilitate fluid drainage through body lumens by including one or more laterally-open channels and a structure that resists collapse due to external pressure.

Figure 1:
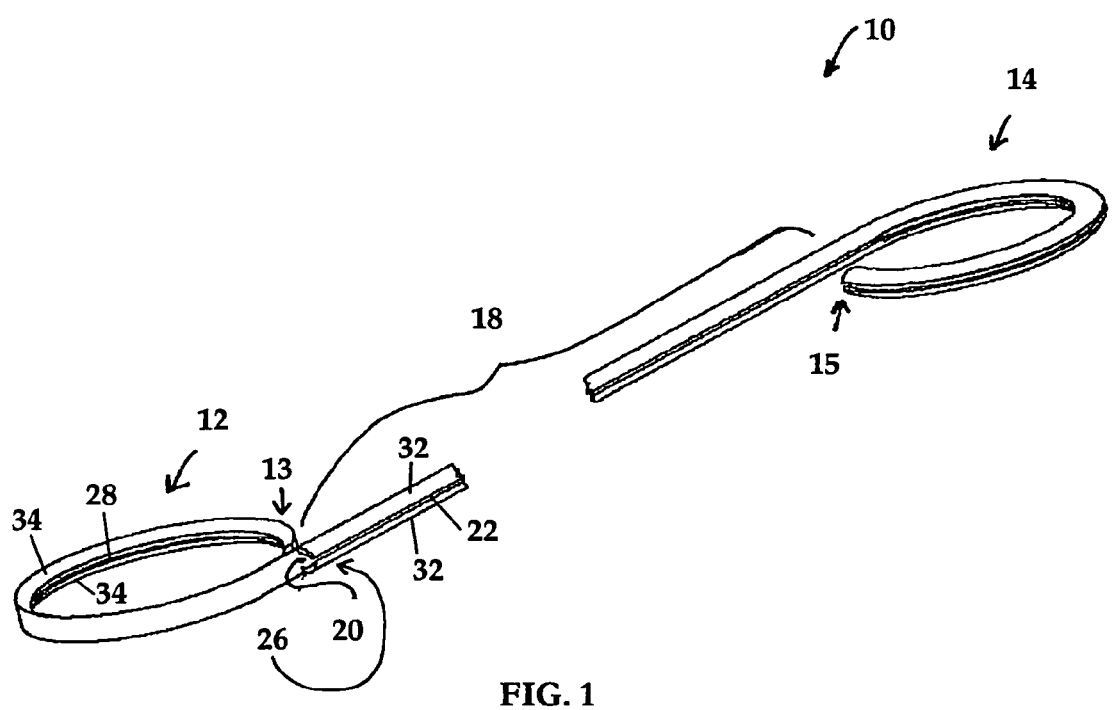
FIG. 1 is a perspective view of an exemplary embodiment of a stent according to the present disclosure.

FIG. 1 shows one exemplary embodiment of such a stent in perspective. The depicted stent 10 features a flexible, elongate body including a curled proximal portion 12 having a proximal tip 13, a curled distal portion 14 having a distal tip 15, and a main portion 18 extending between the proximal and distal portions.

The proximal and distal portions are curled so that they can be anchored in anatomic sites, while the main portion is so sized and shaped as to fit in a selected body lumen. In preferred embodiments, the proximal and distal portions are each curled through at least 180 degrees, and preferably curled through at least 270 degrees. Such curling improves the portions' anchoring ability while lessening the chance that the ends of the stent will contact and irritate their respective anatomic sites.

The main and distal portions define a channel 20 that is laterally open along at least a part of its length and extends along the main and distal portions without extending along the proximal portion. Thus, the channel's proximal end 26 is disposed in the main portion 18.

The channel is defined at least in part by flanges 32 that curve toward one another, leaving a gap 22 between them. The gap is so sized, in preferred embodiments, as to enable the channel to contain an object that cannot be laterally removed from the channel without expanding the gap. For example, the gap width may be less than or equal two half of the channel's diameter (the "channel's diameter" being defined as the diameter of the largest circle that can fit inside the channel without deforming the stent), more preferably between about one fifth and about one half of the channel's diameter, and most preferably between about one fourth and about one third of the channel's diameter.

The proximal, main, and distal portions define a second channel separate from the previously mentioned, first channel 20, along the other side of the body; this second channel 24 is also defined at least in part by flanges 34, leaving a gap 28 between them. The stent is typically manufactured by extrusion.

Figure 2:
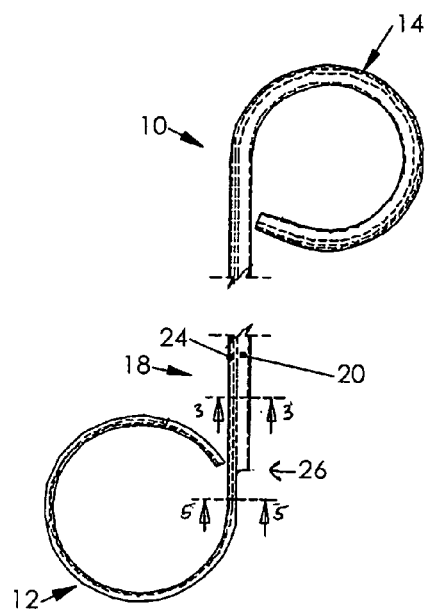
FIG. 2 is a plan view of the stent shown in FIG. 1.

FIG. 2 shows a plan view of the exemplary embodiment from FIG. 1. In this view, the first channel 20 and the second channel 24 are indicated by broken lines. The proximal portion 12 contains less material per unit length than the stent's other portions do, because the portions of the flanges that define the first channel do not extend into the proximal portion.

Figure 3:
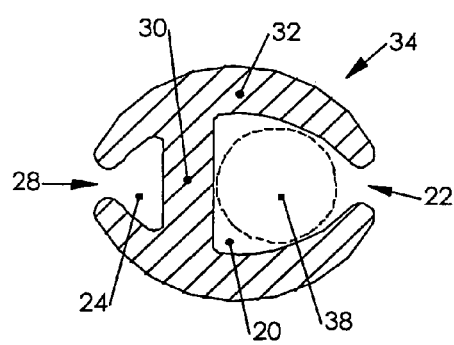
FIG. 3 is a cross-sectional view of the stent shown in FIG. 2, taken at cut line 3—3.

FIG. 3 shows a cross-section view of the stent 10 taken in the main portion 18 at cut line 3—3 of FIG. 2. The stent has an I-beam shape, including a web 30 and two flanges 32 extending from opposite ends of the web. The I-beam shape gives the stent strength and structural integrity. Furthermore, the sides of the web and the flanges together define the first channel 20 and the second channel 24. In this rest position, the flanges' tips typically do not touch each other; they leave gaps or lateral openings 22, 28 for the first and second channels, respectively. The first channel is typically so sized as to accommodate a guidewire 38.

Figure 4:
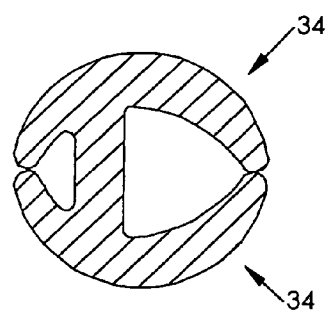
FIG. 4 is a cross-sectional view of a compressed stent.

In preferred embodiments, the flanges curve toward each other. Curved flanges improve comfort for the recipient and reduce trauma to the body lumen by providing smooth surfaces uninterrupted by sharp edges. The curved flanges also help prevent the stent from collapsing due to external pressure. As shown in FIG. 4, when the stent is externally compressed, the lateral edges 34 of the flanges may contact each other, thereby closing the channels' lateral openings. Although the channels are closed to the outside, their interiors are locked open, because the flanges buttress each other. Consequently, the stent may continue to drain fluid through a body lumen, even in the presence of compressive forces.

Figure 5:
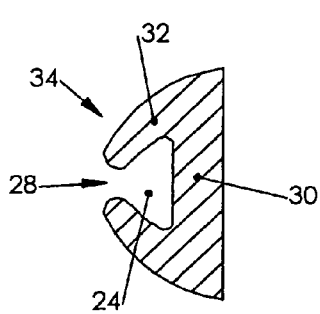
FIG. 5 is a cross-sectional view of the stent shown in FIG. 2, taken at cut line 5—5.

FIG. 5 shows another cross-section view of the stent 10 of FIG. 2, taken in the proximal portion 12 at the cut line 5—5. The parts of the flanges that define the first channel in the main and distal portions do not extend into the proximal portion. Rather, the proximal portion includes the web 30 and the parts of the flanges that define the second channel 24. The edges of the web may be rounded to minimize trauma.

Figure 6:
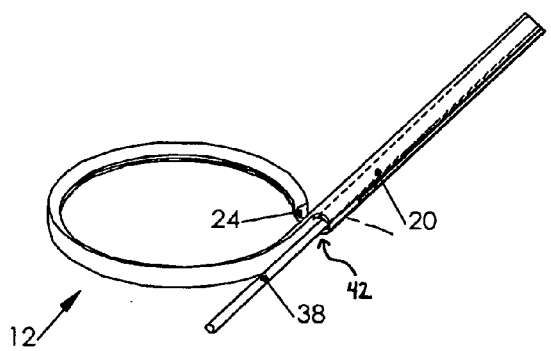
FIG. 6 is a perspective view of the stent shown in FIG. 1 with a guidewire partially inserted.
Figure 7:
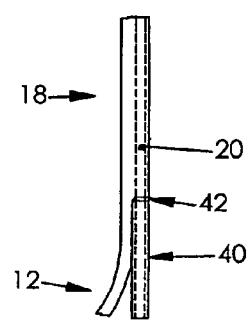
FIG. 7 is a plan view of a portion of the stent shown in FIG. 6 with a pusher in place.

This configuration offers several advantages, some of which are illustrated in FIGS. 6 and 7. First, omitting the first channel from the proximal portion leaves a clearly defined entry point 42 for the first channel in the main portion of the stent body. The opening is easily accessible because the proximal portion need not be uncurled to gain access, and because the flat web provides a guide surface leading up to the opening. This helps a user position a guidewire in the first channel. The clearly defined entry point 42 also provides a mating surface for a pusher 40 that can be used to advance a stent along a guidewire 38. In addition, the exposed web provides a continuation of the first channel's inner wall, which improves fluid flow by reducing the fluid's contact angle. Moreover, removing the first channel in the proximal portion helps prevent fluid stagnation in the proximal portion and inhibits clogging. Furthermore, the proximal portion is less bulky, so it can be more comfortable once it is positioned.

Figure 7A:
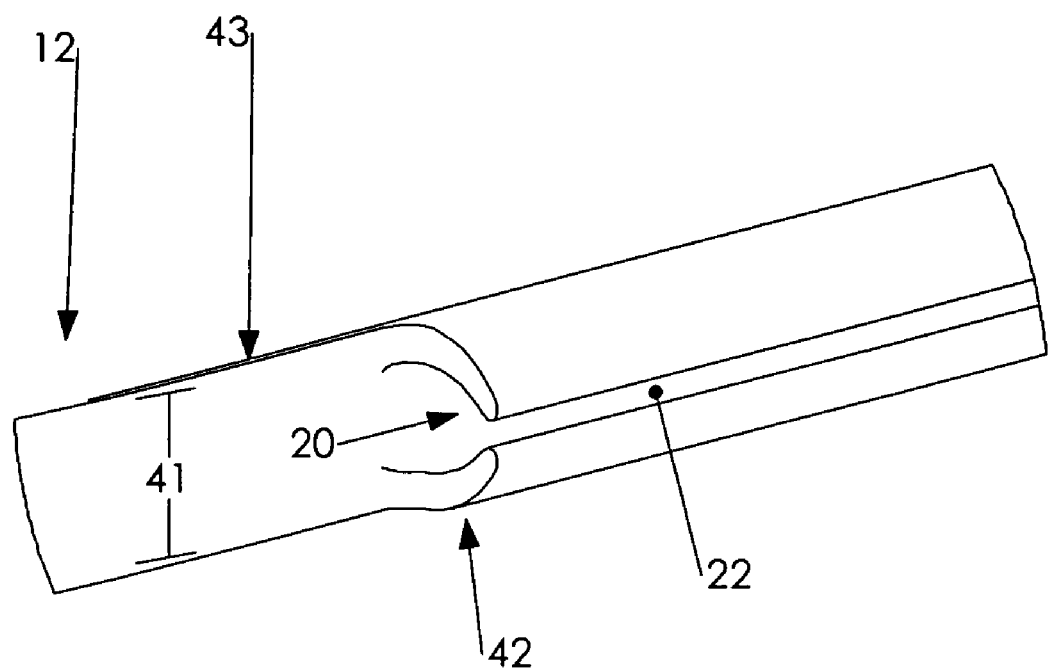
FIG. 7A is a perspective view of an alternative embodiment of a stent.

FIG. 7A provides a partial view of an alternative embodiment of a stent in which the first channel continues into the proximal portion 12, but in such a way as to preserve several of the advantages described above. In this embodiment, the gap 22 in the main and distal portions is so sized as to enable the channel to contain an object that cannot be laterally removed from the channel without expanding the gap. The first channel is laterally open in at least a part of the channel's length in the proximal portion, so that flange edges 43 define a proximal lateral gap 41. The proximal lateral gap 41 is wider than gap 22 to permit at least some objects that fit in the channel to be laterally removed without expanding the proximal lateral gap. In preferred embodiment, the proximal lateral gap 41 is at least 50% wider than gap 22.

In one exemplary use, a stent is positioned in the ureter, a body lumen that extends from the kidney to the urinary bladder. The distal portion is positioned in the kidney, the proximal portion is positioned in the urinary bladder, and the main portion runs through the ureter. This arrangement is shown, for example, in FIG. 15 of U.S. Pat. No. 6,214,037, which patent is hereby incorporated herein in its entirety by this reference.

The stents are typically advanced into position, and removed from position, on guidewires that are inserted in the first channel 20. Although in some preferred embodiments, the channel's lateral gap 22 is so sized as to prevent the guidewire from laterally slipping out of the channel, it is desirable in some instances to provide additional features to help retain the guidewire in the channel. FIGS. 8–16 depict a variety of such features.

Figure 8:
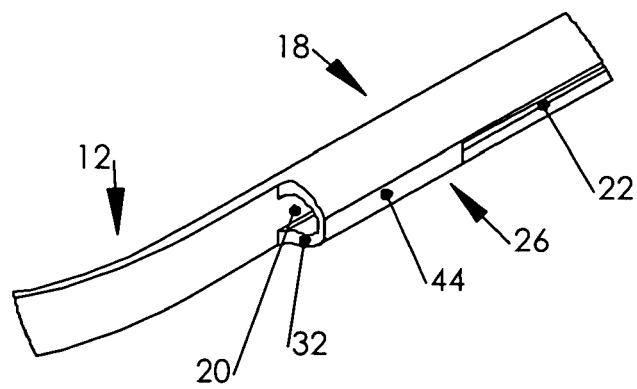
FIGS. 8–16 depict various alternative embodiments of stents having fusings and/or closings.

FIG. 8 depicts a stent in which the proximal end 26 of the channel 20 has a closed portion 44 which laterally closes a portion of the proximal end. The channel's lateral gap 22 continues in other portions of the stent, so the closed portion 44 does not significantly impair lateral fluid flow out of the stent. However, the closed portion 44 significantly helps retain a guidewire in the channel because it keeps the guidewire from prying out of the proximal end's side. In preferred embodiments, the channel is laterally closed along less than about 2 inches of its proximal end, more preferably along less than about 1 inch of its proximal end, and most preferably along at least about ⅛ inch but less than about 1 inch of its proximal end.

Figure 12:
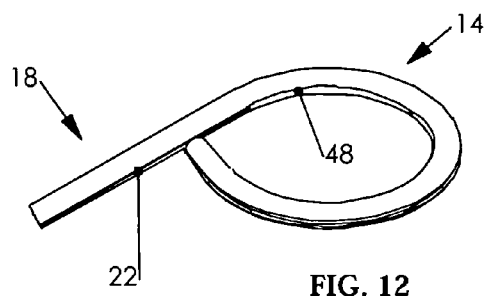

The channel in the distal portion 14 of the stent may also have a closed portion 48, as shown in FIG. 12. In some embodiments, the majority or even the entirety of the channel's length in the distal portion may be closed, as shown in FIG. 12, in order to prevent the stent from buckling off the guidewire. Closing the majority of the channel's length in the distal portion does not interfere with fluid drainage, because it is the ureter that is being stented open, not the kidney.

Figure 11:
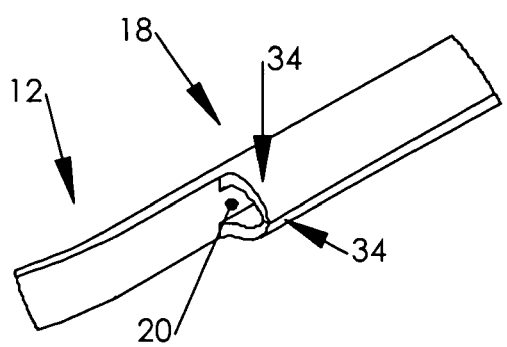
Figure 13:
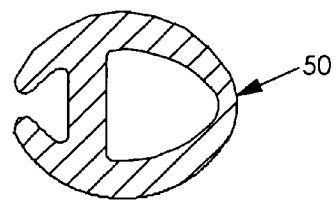

As shown in FIG. 13, the closed portion may be a formed by fusing together the lateral portions of the flanges to form a continuous bridge 50. The flanges may be fused using a variety of techniques, such as melting, bonding, welding, stitching, tying, and other methods. Alternatively, the stent may be initially manufactured with a continuous bridge along the channel's length, which is later sliced open (such as shown in FIG. 11), or opened by having a strip cut out to create the gap.

Figure 9:
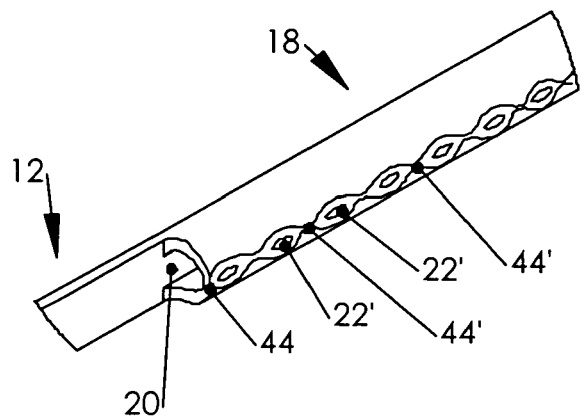
Figure 10:
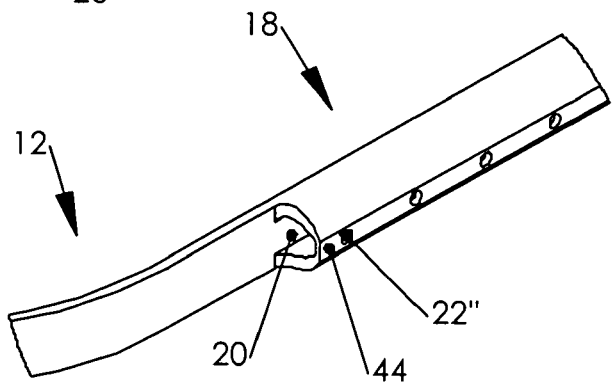

Lateral closures need not be confined to the proximal end. For example, as shown in FIG. 9, the channel may have alternating sections of laterally opened portions 22' and laterally closed portions 44'. Alternatively, as shown in FIG. 10, a stent may define apertures 22'' disposed along the length of the channel, which is otherwise laterally closed. The apertures may, for example, be slits or holes cut in the side of the channel. It is preferred that most of the main portion of the stent's body be laterally open so that the stent permits as much lateral fluid flow as practicable. In preferred embodiments, therefore, the channel is laterally closed along at most about 25% of its length, and more preferably along at most about 10% of its length.

Figure 14:
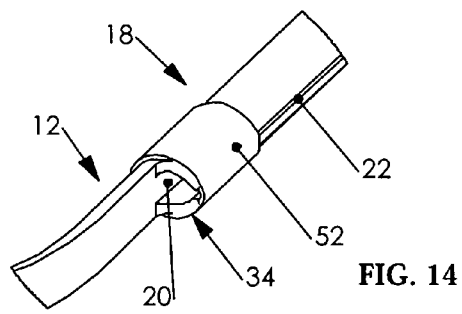

A lateral closing may also be formed by placing a band around the circumference of the stent's body at a selected position. An example of this is shown in FIG. 14, in which a band 52 is placed around the stent at the proximal end 26 of the channel 20 to close the gap 22 at the proximal end. The band can have a variety of widths to provide lateral closings of desired sizes. In preferred embodiments, the band is less than about 1 inch wide and thereby closes less than about 1 inch of the proximal end of the channel when appropriately positioned. The band may be fused to the body of the stent to secure in place, or otherwise affixed, such as by techniques mentioned above. In addition, a stent may include a plurality of bands secured around the circumference of the body, each band thereby forming a laterally closed part of the channel.

Figure 15:
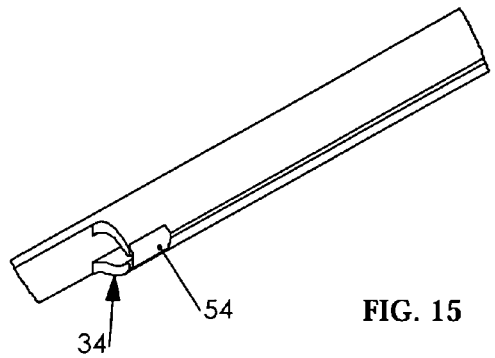
Figure 16:
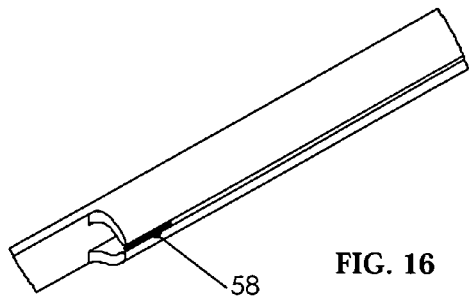

In a similar embodiment, shown in FIG. 15, a patch 54 may applied to the stent's body to create a laterally closed portion of the channel. In other embodiments, the lateral portions of the flanges can both be affixed to a bridge material 58, as shown in FIG. 16. The various features for laterally closing the channel may, of course, be used in various combinations as appropriate for a selected application or as dictated by manufacturing preferences.

Figures 17, 18, 19, 20:
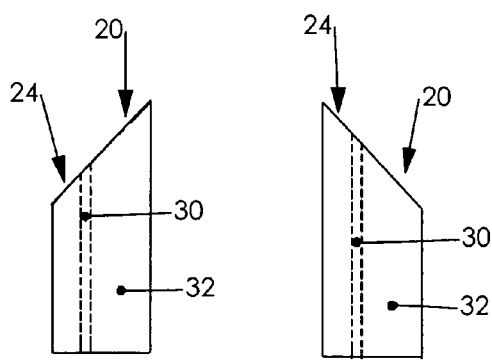
FIGS. 17–21 depict various alterative embodiments of stents having bevelings.
Figure 21:
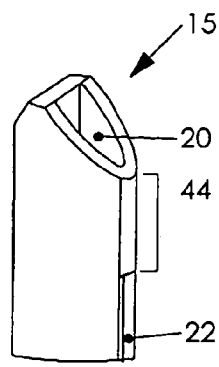

The ends of the stent may be beveled in a variety of ways, some of which are illustrated in FIGS. 17–21. A stent's end may be beveled so that the edge leads toward the first channel (FIG. 17) or the second channel (FIG. 18). The end may have two bevels, as shown in FIG. 19, so that the end is blunted. Beveling may, of course, be combined with other features disclosed herein. For example, FIG. 20 shows an elevation view of a stent having its distal end beveled toward the first channel having a fused lateral opening, while FIG. 21 depicts a stent having a fused first channel end and a double bevel.

Figure 22:
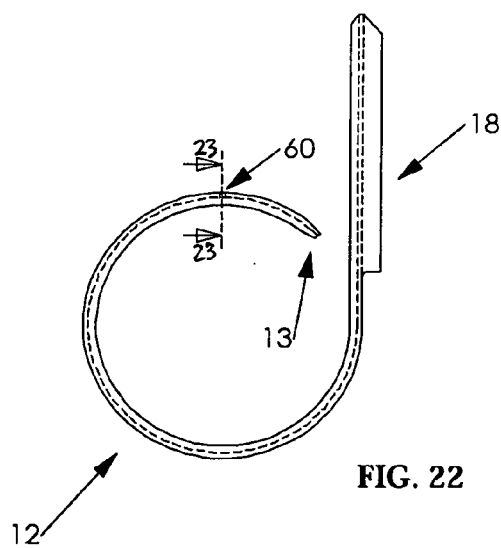
FIGS. 22–23 depict an exemplary embodiment of a stent having a hole for a pull filament.

The ends of the stent may also be tapered. For example, as shown in FIG. 22 the proximal tip 13 may be tapered. Similarly, as shown in FIG. 12, the distal tip may be tapered. A tip can be tapered in a variety of ways, such as by turning it on a grinder, or by inserting the tip in a funnel and melting the tip slightly so that it flows into the funnel's reduced diameter.

Figure 23:
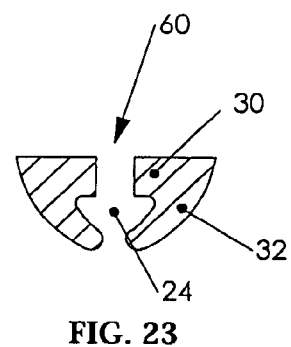

The embodiment shown in FIG. 22 also defines a hole 60 in the proximal portion 12 for receiving a pull string. FIG. 23, a cross-section taken at cut line 23—23, shows the hole 60 more clearly. In this exemplary embodiment, the proximal portion 12 includes the web 30 and flanges 32, thereby defining the second channel 24. The hole is formed in the web 30, so that an opening is created through the full thickness of the stent. A pull string, such as a suture, may be secured in the hole. In some embodiments, the hole has a diameter of about 0.005 inches to about 0.020 inches, or large enough to accommodate standard 3-0 (roughly 0.010") or 4-0 (roughly 0.007") suture, but otherwise be as small as possible for strength. In preferred embodiments, the hole is placed at least ¼ inch from the proximal tip so that the curled proximal end straightens out when the suture is pulled, yet is not so close to the edge that the suture breaks through the stent.

Figure 24:
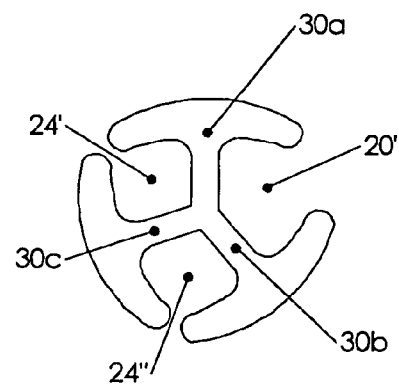
FIG. 24 is a cross-sectional view of an exemplary embodiment of a stent having three open lumens.

FIG. 24 illustrates an alternative embodiment of a stent, in which the body defines three channels 20', 24', and 24". The web has three components 30*a*, 30*b,* and 30*c* which, together with the flanges, define the channels. Additional channels may be defined by forming stents with webs having additional components.

EXAMPLES

Example 1

Ureteral Stent

Ureters typically have convoluted shapes because their walls include many folds. These folds can capture stones, and thus create obstructions. The folds can also unfold to dilate the ureter. Accordingly, stents are typically sized to facilitate the ureter's dilation.

Ureteral stents are typically 3.7, 4.0, 5.0, 6.0, 7.0, 8.0, 8.5, and 9.0 French (1.23–3 mm, with "French" being a unit of measure that equals ⅓ mm exactly or roughly 0.01312 inches). The most common sizes by far are 6.0 and 7.0 Fr, because they best balance the competing demands of providing as much flow as possible through the ureter while also being able to fit into the ureter's tight space. Lengths run from 20–30 cm typically in 2 cm gradients. Stents for pediatric use can be smaller, both in length and diameter.

The ureteral stent resembles the stent shown in FIGS. 1–3, in that it has an I-beam cross section that defines two channels, the first channel larger than the other. Sizes were selected so that the larger lumen fit over a 0.038 inch guidewire but that the stent still had an overall outer diameter of 6F along one axis (when compressed) and 7F along the perpendicular axis. The larger lumen is typically given a diameter slightly larger than the desired guidewire so that the guidewire has some clearance but is not so loose that it slips out easily. For example, the diameter of the larger lumen may be in the range 0.039 to 0.050 inch to accommodate an 0.038 inch guidewire, preferably about 0.041 inch. The second, smaller, lumen may be sized to accommodate, for example, an 0.025 inch or 0.018 inch guidewire.

Accordingly, the web is off-center so that the larger lumen can accommodate the guidewire without making the stent too large to fit easily in the ureter and in typical introducer catheters, which have a 7F working channel. The flanges are curved to fit best into the ureter's tight lumen and be less irritating to the body.

The ureteral stent may be made of a variety of materials, most typically polyurethanes, polyethylene or silicone. For silicone, the web is typically 0.020–0.030 inch thick. Polyurethane is stronger than silicone, and the web can be 0.014 to 0.020 inch thick. In a preferred embodiment, the web is 0.016 inch (0.41 mm) thick.

Stents are typically made as soft as possible for the recipient's comfort. In addition, FDA guidelines provide that the stent must traverse around a 2" radius without kinking. However, it is easier to direct stents that have enough stiffness that they do not collapse during insertion. Accordingly, a hardness durometer range of 50A–95A is typical, with silicone being on the lower end and polyurethane on the upper end.

It is preferred that the gap be as large as possible between the flanges, to achieve the greatest possible flow, but it should not be so large as to let the guidewire pop out the side naturally or under pressure. In preferred embodiments, the gaps may be about 0.003 inch to about 0.018 inch, more preferably 0.010" to 0.012". The preferred maximum is less than half the diameter of the typical 0.038" guidewire. In some embodiments, the width of the gap between the flange edges is between about one fifth and about one half of the channel's diameter, more preferably between about one fourth and about one third of the channel's diameter.

In preferred embodiments, the first, larger, channel is defined in the main and distal portions of the stent, but does not extend into the proximal portion; i.e., the large channel is "cut away" from the proximal portion. Moreover, the proximal portion is curled away from the opining of the larger lumen to facilitate access to the main lumen, as discussed above. In the ureteral stent, the cutaway is located slightly below where the stent would enter the junction between the bladder and the ureter (the uretero-vesical junction, or UVJ), typically about 0.25" below a line marked on the stent to indicate the expected UVJ position. The small distance is provided so that the edge of the cutaway does not the sensitive UVJ opening. With less material, the partial bladder coil may also be more comfortable in the bladder. The curled proximal portion curls through at least 270 degrees around so that there is no sharp end poking into the bladder. In preferred embodiments, the proximal and distal portions are curled to have a curl diameter in the range of about 0.4 to about 1.0 inch, preferably about 0.65 inch, so that the curls are firm enough not to have the stent slip out, but compliant enough so the flanges do not buckle and crease with a tight turn and so the coil will not spontaneously spring off a guidewire.

The proximal end of the larger lumen is closed to prevent the guidewire from popping out, as described above. The preferred closed length is between about ⅛ inch and about 1.0 inch. On the distal, renal, tip, the entire distal portion may be closed to protect the kidney from guidewire injury. For a distal portion having a 0.65 inch diameter curl through about 270 degrees, about 1.5 inches of the distal portion would be closed. Portions may be closed by fusing, patching, filling, banding, or by other methods described above.

There are markings along the length of the device for the urologist to see the progression of the stent up the ureter through the cystoscope. The markings are typically 5 cm apart with another marking at the UVJ.

Other materials from which the stent may be formed include polyvinyl chloride (PVC), urethane and polyethylene oxide. In addition, the stent may be formed of a coated metal, such as nickel-titanium alloy coated with plastic, Dacron, polyimide, or the like. The stent can also have other coatings/top layer like Dacron, Polyimide to prevent encrustation or be for slipperiness. Hydrogels are hydrophilic polyurethane polymer coatings that provide slipperiness for insertion. Examples of hydrogels include non-ionic synthesized hydrogels, such as polyacrylamide, polyvinyl alcohol, polyethylene glycol, poly-N-vinyl-pyrrolidone and poly-methoxy-peg methacrylate. Ionic hydrogels include crosslinked polyacrylamide-acrylic acid and polyacrylamide-dimethyl-aminoethyl methacrylate copolymers.

Example 2

Biliary Stent

Figure 25:
FIGS. 25–27 depicts embodiments of stents having barbs.
Figure 26:
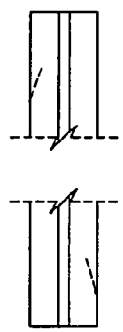
Figure 27:
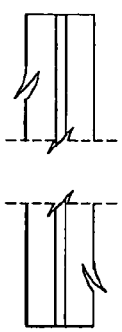

Biliary stents are typically 4.0, 5.0, 6.0 7.0, 8.5, 10.0, and 11.5 French in diameter and 5, 7, 9, 12, and 15 cm long. A biliary stent may have a V cut into the stent and pulled out to form a barb to hold it in place, such as shown in FIGS. 25–27. The larger lumen is typically sized to accommodate an 0.035 inch guidewire. Either or both the proximal and distal portions may be curled.

Example 3

Pancreatic Stent

Pancreatic stents may be 5.0, 7.0, 10.0 F with 1" between the barbs, and be 3.0, 5.0, 7.0, 12.0 cm in length. A pancreatic stent may have a V cut into the stent and pulled out to form a barb to hold it in place, such as shown in FIGS. 25–27. The larger lumen is typically sized to accommodate an 0.035 inch guidewire. Either or both the proximal and distal portions may be curled.

In addition to placement in a ureter, stents may be so sized and shaped to relieve and prevent obstruction in other body lumens, including airways, the bowel, blood vessels, ear canals, breast ducts, lacrimal ducts, hepatic ducts, lymph ducts, the urethra, and others.

What is claimed is:

1. A stent comprising a flexible, elongate body having a curled proximal portion, a curled distal portion, and a main portion extending between the proximal and distal portions, wherein;
   A) the main and distal portions together define a channel laterally open throughout at least a part of the channel's length and extending along the main and distal portions without extending along the proximal portion, whereby the channel's proximal end is disposed in the main portion;
   B) the channel is laterally closed along less then about 2 inches of its proximal end; and
   C) the proximal portion is curled away from the channel.

2. The stent of claim 1, wherein the channel is laterally closed along at least about 10% of the channel's length.

3. The stent of claim 1, wherein the channel is laterally closed along at least about 25% of the channel's length.

4. The stent of claim 1, wherein the channel is laterally closed along less than about 1 inch of its proximal end.

5. The stent of claim 1, wherein the channel is laterally closed along at least about 0.125 inches, but less than about 1 inch, of its proximal end.

6. The stent of claim 1, wherein the main portion of the body comprises a web and two flanges extending from opposite ends of the web.

7. The stent of claim 6, wherein the two flanges curve toward each other.

8. The stent of claim 6, wherein the two flanges each have lateral edges, and the lateral edges of the respective flanges, in at least one rest position, do not touch each other along the at least one laterally open part of the channel.

9. The stent of claim 6, wherein the channel is defined by a side of the web and lateral portions of the two flanges.

10. The stent of claim 9, wherein the two flanges each have lateral edges, and the lateral edges of the respective flanges, in at least one rest position, do not touch each other along the at least one laterally open part of the channel, leaving a gap therebetween.

11. The stent of claim 10, wherein the width of the gap between the flange edges is less than half of the channel's diameter.

12. The stent of claim 10, wherein the width of the gap between the flange edges is between about one fifth and about one half of the channel's diameter.

13. The stent of claim 10, wherein the width of the gap between the flange edges is between about one fourth and about one third of the channel's diameter.

14. The stent of claim 9, wherein the at least one laterally open part of the channel is defined by an aperture cut in the at least one laterally closed part of the channel.

15. The stent of claim 9, further comprising a band placed around the circumference of the body to form the at least one laterally closed part of the channel.

16. The stent of claim 9, wherein at least a part of the channel in the distal portion is laterally closed.

17. The stent of claim 16, wherein substantially the entire length of the channel in the distal portion is laterally closed.

18. The stent of claim 1, wherein the proximal portion is curled through at least 180 degrees.

19. The stent of claim 1, wherein the proximal portion is curled through at least 270 degrees.

20. The stent of claim 1, wherein the distal portion is curled through at least 270 degrees.

21. The stent of claim 1, wherein the channel is so sized as to accommodate a guidewire having a diameter of 0.038 inches.

22. The stent of claim 1, wherein the main and distal portions together define a second channel separate from the previously mentioned, first channel, the second channel being laterally open throughout at least a part of the second channel's length and extending along the main and distal portions.

23. The stent of claim 22, wherein the proximal portion also defines the second channel.

24. The stent of claim 22, wherein the first channel is larger than the second channel.

25. The stent of claim 22, wherein the main portion of the body comprises a web and two flanges extending from opposite ends of the web, the first channel is defined by a side of the web and lateral portions of the two flanges extending on the side of the web, and the second channel is defined by an opposite side of the web and lateral portions of the two flanges extending on the opposite side of the web.

26. The stent of claim 25, wherein the web defines a plurality of perforations connecting the first channel and the second channel.

27. The stent of claim 1, so sized as to be deployable in a ureter.

28. The stent of claim 1, so sized as to be deployable in a bile duct.

29. The stent of claim 1, so sized as to be deployable in a pancreatic duct.

30. The stent of claim 1, wherein the end of the proximal portion is tapered.

31. The stent of claim 1, wherein the end of the distal portion is tapered.

32. The stent of claim 1, wherein the end of the distal portion is beveled.

33. The stent of claim 1, wherein the proximal portion defines a hole so sized as to secure a pull string.

34. The stent of claim 33, wherein the hole is positioned within 0.25 inches of the end of the proximal portion.

35. The stent of claim 1, further comprising a band placed around the circumference of the body to laterally close at least a part of the channel's length.

36. The stent of claim 1, wherein:
   A) the main and distal portions together define a second channel separate from the previously mentioned, first channel, the second channel being laterally open throughout at least a part of the second channel's length and extending along the main and distal portions;
   B) the proximal portion is curled away from the channel through at least 270 degrees; and
   C) the stent further comprises a band placed around the circumference of the body to form the at least one laterally closed part of the channels.

37. The stent of claim 36, wherein the distal end of the distal portion is beveled.

38. The stent of claim 1, wherein at least one laterally open part of the channel is defined by an aperture cut in a laterally closed part of the channel.

39. The stent of claim 1, wherein the channel is laterally closed along at least about 0.125 inches of its proximal end.

40. A method of manufacturing a stent as defined by claim 1 comprising:
   extruding the stent; and
   cutting an aperture in the channel to define the laterally open part of the channel.

41. A stent comprising a flexible, elongate body having a curled proximal portion, a curled distal portion, and a main portion extending between the proximal and distal portions, wherein:
   A) the main and distal portions together define a channel laterally open throughout at least a part of the channel's length and extending along the main and distal portions without extending along the proximal portion, whereby the channel's proximal end is disposed in the main portion;
   B) a band is placed around the circumference of the body to laterally close no more than about 1 inch of the channel's proximal end; and
   C) the proximal portion is curled away from the channel.

42. A stent comprising a flexible, elongate body having a curled proximal portion, a curled distal portion, and a main portion extending between the proximal and distal portions, wherein:
   A) the main and distal portions together define a channel laterally open throughout at least a part of the channel's length and extending along the main and distal portions without extending along the proximal portion, whereby the channel's proximal end is disposed in the main portion;
   B) the main portion of the body comprises a web and two flanges extending from opposite ends of the web
   C) the channel is defined by a side of the web and lateral portions of the two flanges;
   D) the lateral portions of the two flanges are fused together to close the at least one laterally closed part of the channel; and
   E) the proximal portion is curled away from the channel.

43. A stent comprising a flexible, elongate body having a curled proximal portion, a curled distal portion, and a main portion extending between the proximal and distal portions, wherein;
   A) the main and distal portions together define a channel laterally open throughout at least a part of the channel's length and extending along the main and distal portions without extending along the proximal portion, whereby the channel's proximal end is disposed in the main portion;
   B) the main portion of the body comprises a web and two flanges extending from opposite ends of the web
   C) the channel is defined by a side of the web and lateral portions of the two flanges;
   D) the two flanges each have lateral edges, and the lateral edges of respective flanges are both fused to a bridge material between the lateral edges, to close the at least one laterally closed part of the channel; and
   E) the proximal portion is curled away from the channel.

44. A stent comprising a flexible, elongate body having a curled proximal portion, a curled distal portion, and a main portion extending between the proximal and distal portions, wherein:
   A) the main and distal portions together define a channel laterally open throughout at least a part of the channel's length and extending along the main and distal portions without extending along the proximal portion, whereby the channel's proximal end is disposed in the main portion;
   B) the main portion of the body comprises a web and two flanges extending from opposite ends of the web
   C) the channel is defined by a side of the web and lateral portions of the two flanges;
   D) a band is placed around the circumference of the body to form the at least one laterally closed part of the channel;
   E) the band is fused to the flexible elongate body; and
   F) the proximal portion is curled away from the channel.

45. A stent comprising a flexible, elongate body having a curled proximal portion, a curled distal portion, and a main portion extending between the proximal and distal portions, wherein:
   A) the main and distal portions together define a channel laterally open throughout at least a part of the channel's length and extending along the main and distal portions without extending along the proximal portion, whereby the channel's proximal end is disposed in the main portion;
   B) the main portion of the body comprises a web and two flanges extending from opposite ends of the web C) the channel is defined by a side of the web and lateral portions of the two flanges;

D) a plurality of bands is placed around the circumference of the body and fused thereto, each band thereby forming a laterally closed part of the channel; and E) the proximal portion is curled away from the channel.

46. A stent comprising a flexible, elongate body having a curled proximal portion, a curled distal portion, and a main portion extending between the proximal and distal portions, wherein:

A) the main, distal, and proximal portions together define a channel extending along those portions and being laterally open throughout at least a part of the channel's length;

B) the laterally open part of the channel in the main and distal portions defines a lateral gap;

C) the laterally open part of the channel in the proximal portion defines a proximal lateral gap wider than the lateral gap; and D) the proximal portion is curled away from the channel.

47. The stent of claim 46, wherein the proximal lateral gap is at least 50% wider than the lateral gap.

\* \* \* \* \*